United States Patent
Nakamura

(10) Patent No.: US 8,416,542 B2
(45) Date of Patent: Apr. 9, 2013

(54) ELECTRONIC DEVICE

(75) Inventor: Masatsugu Nakamura, Yokohama (JP)

(73) Assignee: Kyocera Corporation, Kyoto (JP)

( * ) Notice: Subject to any disclaimer, the term of this patent is extended or adjusted under 35 U.S.C. 154(b) by 0 days.

(21) Appl. No.: 13/130,776

(22) PCT Filed: Nov. 25, 2009

(86) PCT No.: PCT/JP2009/006354
§ 371 (c)(1), (2), (4) Date: Aug. 3, 2011

(87) PCT Pub. No.: WO2010/061593
PCT Pub. Date: Jun. 3, 2010

(65) Prior Publication Data
US 2011/0279931 A1    Nov. 17, 2011

(30) Foreign Application Priority Data

Nov. 26, 2008 (JP) .................................. 2008-301750

(51) Int. Cl.
*H02H 9/02* (2006.01)
(52) U.S. Cl. ......................................... 361/42; 361/93.1
(58) Field of Classification Search .................... 361/42, 361/52, 93.1; 324/681, 694
See application file for complete search history.

(56) References Cited

U.S. PATENT DOCUMENTS

| | | | |
|---|---|---|---|
| 2006/0208914 A1* | 9/2006 | Liu et al. | 340/620 |
| 2012/0038374 A1* | 2/2012 | Johnson | 324/694 |
| 2012/0218673 A1* | 8/2012 | Oguri | 361/93.1 |
| 2012/0293193 A1* | 11/2012 | Sheu et al. | 324/694 |

FOREIGN PATENT DOCUMENTS

| | | | |
|---|---|---|---|
| JP | 8324912 A | 12/1996 | |
| JP | 2004235724 A | 8/2004 | |
| JP | 2005311637 A | 11/2005 | |
| JP | 2007251830 A | 9/2007 | |

* cited by examiner

*Primary Examiner* — Danny Nguyen
(74) *Attorney, Agent, or Firm* — Hoffman & Baron, LLP

(57) ABSTRACT

Disclosed is an electronic device capable of controlling a power supply interrupt according to the state of water leakage. A portable telephone (1) is equipped with a water leakage detection unit (60) that detects a physical quantity which changes according to the state of water leakage and a CPU (49) that interrupts a power supply in response to the detection result from the water leakage detection unit (60). When the electrostatic capacity detected by the water leakage detection unit (60) is greater than or equal to a threshold value A and less than a threshold value B, the CPU (49) continues to interrupt the power supply until a time T1 elapses, and when the electrostatic capacity detected by the water leakage detection unit (60) is equal to or greater than the threshold value B, said CPU continues to interrupt the power supply until a time T2 which is longer than the time T1 elapses.

12 Claims, 6 Drawing Sheets

ELECTRONIC DEVICE

CROSS-REFERENCE TO RELATED APPLICATIONS

This application is the National Stage of International Application No. PCT/JP2009/006354, filed Nov. 25, 2009, which claims the benefit of Japanese Application No. JP 2008-301750, filed Nov. 26, 2008, the contents of all of which are incorporated by reference herein.

TECHNICAL FIELD

The present invention relates to an electronic device that can detect water exposure.

BACKGROUND ART

An electronic device such as a cellular telephone may become damaged due to a short circuit of electronic components installed on a circuit board in a case of minor water exposure, for example when dew condensation is caused on the circuit board inside the electronic device by a rise in environmental temperature from a low temperature to a normal temperature or when the circuit board inside the electronic device gets wet due to rain and the like.

Such an electronic device is more highly likely to become damaged due to a short circuit of electronic components installed on a circuit board in a case of major water exposure, for example when water is poured on the electronic device or the electronic device is submerged in water.

An electronic device has been proposed that prevents breakdown thereof due to water exposure, by interrupting power supply from a battery in a case of detection of water-exposed state (for example, see Cited Publication 1).

[Patent Document 1] Japanese Unexamined Patent Application, Publication No. 2007-251830

DISCLOSURE OF THE INVENTION

Problems to be Solved by the Invention

However, as the electronic device disclosed in Cited Publication 1 interrupts power supply if a water-exposed state is detected, rebooting of the electronic device may be time consuming.

Given this, the present invention is aimed at providing an electronic device which can control interruption of power source according to a water-exposed state.

Means for Solving the Problems

An electronic device according to the present invention includes: a detection unit that detects a physical quantity that changes according to a water-exposed state; and a control unit that interrupts power supply until a first predetermined time period elapses, in a case in which the physical quantity detected by the detection unit is at least a first threshold value and less than a second threshold value, and interrupts the power supply until a second predetermined time period, which is longer than the first predetermined time period, elapses, in a case in which the physical quantity detected by the detection unit is at least the second threshold value.

In addition, it is preferable to include a notification unit that makes a notification in a first mode in a case in which the physical quantity detected by the detection unit is at least the first threshold value and less than the second threshold value, and makes a notification in a second mode in a case in which the physical quantity detected by the detection unit is at least the second threshold value, in which the control unit interrupts power supply after the notification in the first or second mode by the notification unit.

In addition, it is preferable that the control unit prevents interruption of the power supply after the first predetermined time period or the second predetermined time period elapses.

In addition, it is preferable that the control unit continues interruption of the power supply in a case in which the physical quantity detected by the detection unit after the first predetermined time period or the second predetermined time period elapses is at least the first threshold value.

In addition, it is preferable that the detection unit includes a plurality of detection pads, the physical quantity of each of the detection pads changes according to a water-exposed state and a detection sensor that detects a change in the physical quantity of each of the plurality of detection pads.

In addition, it is preferable that the physical quantity is capacitance.

An electronic device according to the present invention includes: a detection unit that detects a water-exposed state; and a control unit that interrupts power supply until a first predetermined time period elapses in a case in which the detection unit detects a first water-exposed state and interrupts power supply until a second predetermined time period, which is longer than the first predetermined time period, elapses, in a case in which the detection unit detects a second water-exposed state, which is greater in degree of the water-exposed state than a first water-exposed state.

In addition, it is preferable to further include a notification unit that makes a notification in a first mode in a case in which the detection unit detects the first water-exposed state, and makes a notification in a second mode in a case in which the detection unit detects the second water-exposed state, in which the control unit interrupts power supply after the notification in the first or second mode by the notification unit.

In addition, it is preferable that the control unit prevents interruption of the power supply after the first predetermined time period or the second predetermined time period elapses.

In addition, it is preferable that the control unit continues interruption of the power supply in a case in which the detection unit detects the first or second water-exposed state after the first predetermined time period or the second predetermined time period elapses.

In addition, it is preferable that the detection unit includes a plurality of detection pads, the physical quantity of each of the detection pads changes according to water-exposed state and a detection sensor that detects a change in the physical quantity of each of the plurality of detection pads.

In addition, it is preferable that the first water-exposed state is a state in which a change in the physical quantity is detected by the detection sensor in all of the plurality of detection pads, and the second water-exposed state is a state in which a change in the physical quantity is detected by the detection sensor in a part of the plurality of detection pads.

EFFECTS OF THE INVENTION

According to the present invention, an electronic device which can control interruption of power source according to a water-exposed state can be provided.

PREFERRED MODE FOR CARRYING OUT THE INVENTION

Figure 1:
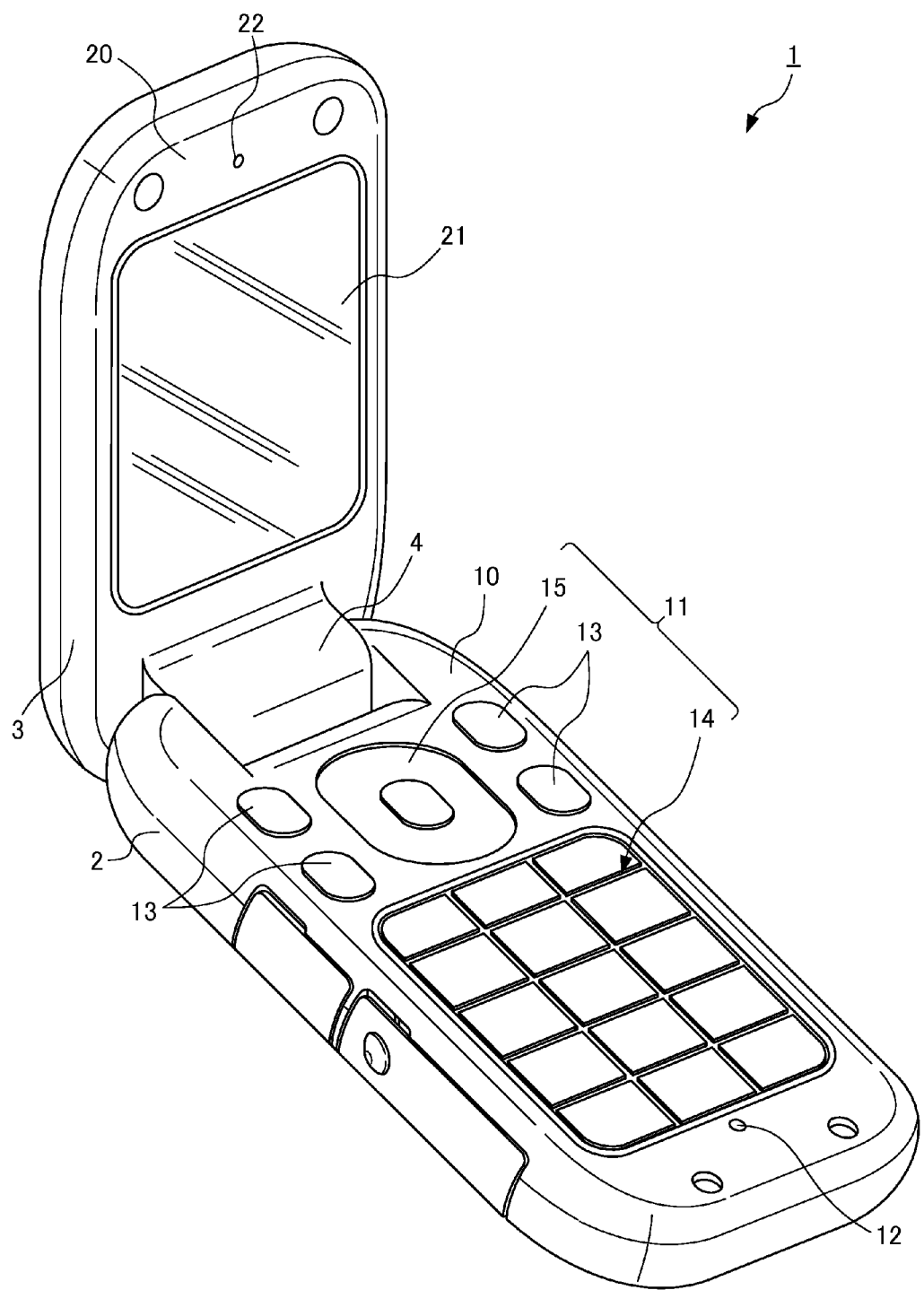
FIG. 1 is a perspective view showing an appearance of a cellular telephone 1 as an example of an electronic device according to the present invention.

An embodiment of the present invention is described hereinafter. FIG. 1 is a perspective view showing an appearance of a cellular telephone 1 as an example of an electronic device according to the present invention. It should be noted that, although FIG. 1 shows a so-called folding type cellular telephone, the present invention is not limited thereto. The cellular telephone 1 may be of, for example: a slider type in which one body slides in one direction from a state in which two bodies are mutually superimposed; a rotating type (turning type) in which one body is rotated about an axis line along the direction in which two bodies are superimposed; or a type in which an operation unit and a display unit are arranged in one body without a connection unit (straight type, flip type).

The cellular telephone 1 is configured to include an operation unit side body 2 and a display unit side body 3. The operation unit side body 2 is configured to include on a front face 10 thereof an operation unit 11 and a microphone 12 to which sounds, which a user of the cellular telephone 1 produces during a phone call, are input. The operation unit 11 includes: feature setting operation buttons 13 for operating various settings and various features such as a telephone number directory feature and a mail feature; input operation buttons 14 for inputting digits of a telephone number and characters for mail; and a selection operation button 15 that performs selection of the various operations and scrolling.

The display unit side body 3 is configured to include, on a front face portion 20, a LCD (Liquid Crystal Display) display unit 21 for displaying a variety of information, and a speaker 22 for outputting sound of the other party of the conversation.

An upper end portion of the operation unit side body 2 and a lower end portion of the display unit side body 3 are connected via a hinge mechanism 4. The cellular telephone 1 can be in a state where the operation unit side body 2 and the display unit side body 3 are apart from each other (opened state), and in a state where the operation unit side body 2 and the display unit side body 3 are contacting each other (folded state), as the operation unit side body 2 and the display unit side body 3, connected via the hinge mechanism 4, pivot with respect to each other.

Figure 2:
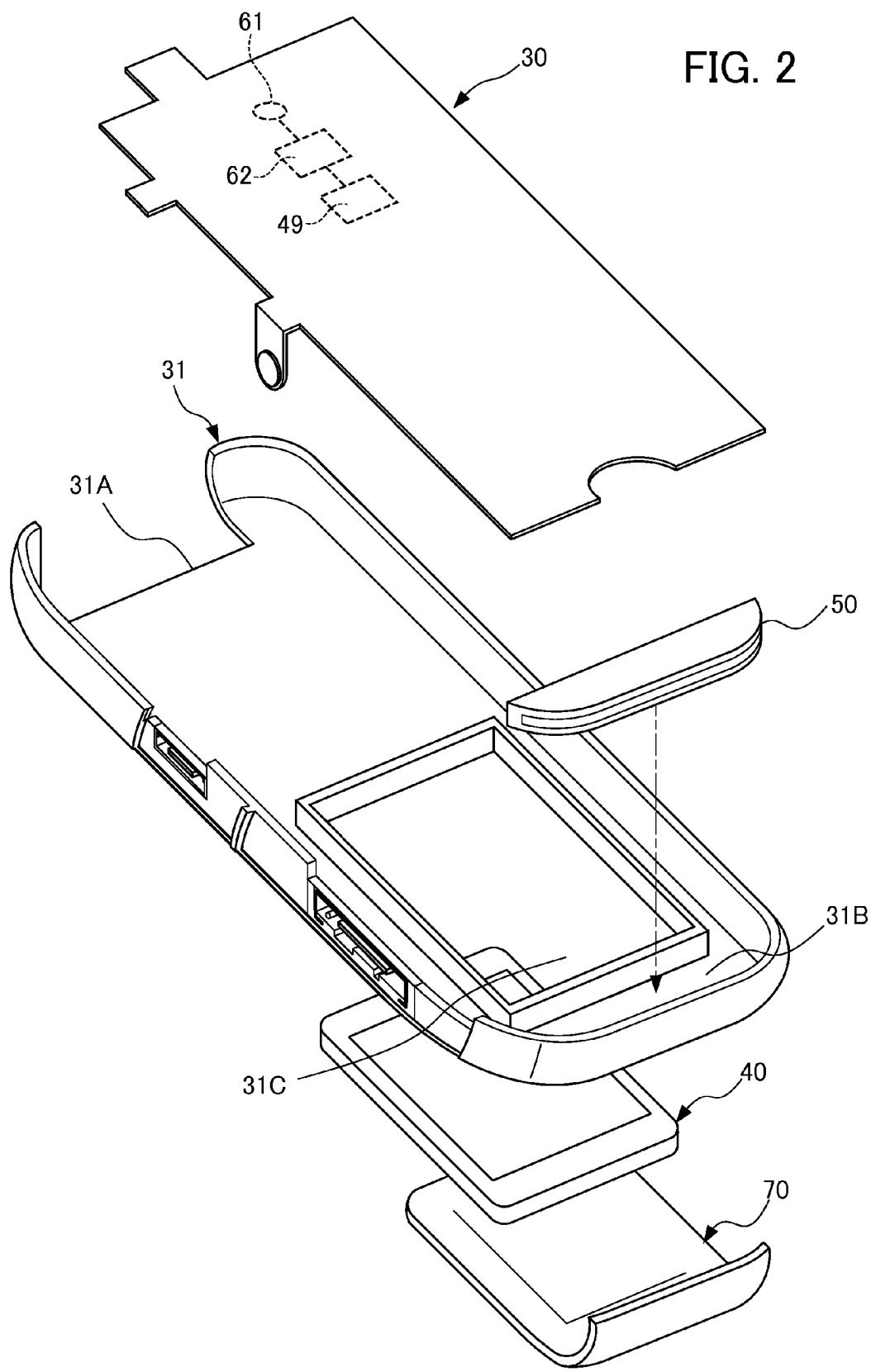
FIG. 2 is an exploded perspective view of a part of the operating unit side body 2.

In addition, FIG. 2 is an exploded perspective view of a part of the operating unit side body 2. As shown in FIG. 2, the operation unit side body 2 is configured such that a circuit board 30 (see FIG. 3), a rechargeable battery 40, a main antenna 50 and the like are housed in a rear case portion 31. In addition, the rechargeable battery 40 is covered by a rechargeable-battery cover (battery lid) 70 that is removable.

Figure 3:
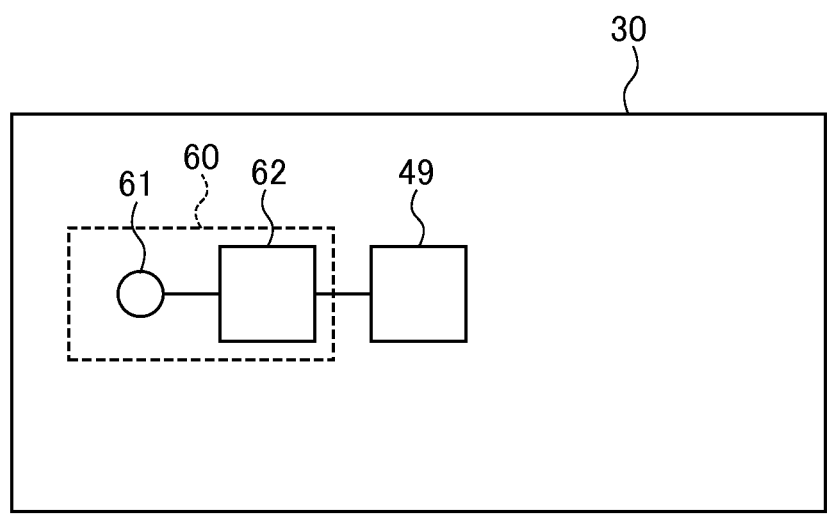
FIG. 3 is a plan view showing a configuration of a circuit board 30.

As shown in FIGS. 2 and 3, the circuit board 30 has an element such as a CPU 49 for performing predetermined arithmetic processing being installed on a face thereof facing the rechargeable battery 40, and a predetermined signal is provided to the CPU 49 when a user operates the operation unit 11 on the front face 10. The circuit board 30 also has a water exposure detection unit 60, provided with a detection pad 61 and a detection sensor 62, being installed thereon as an electronic component.

The rear case portion 31 includes: a hinge mechanism fixing portion 31A that fixes the hinge mechanism 4; a main antenna housing portion 31B that houses a main antenna 50 which communicates using a predetermined usable frequency band; and a rechargeable-battery housing portion 31C that houses the rechargeable battery 40.

Figure 4:
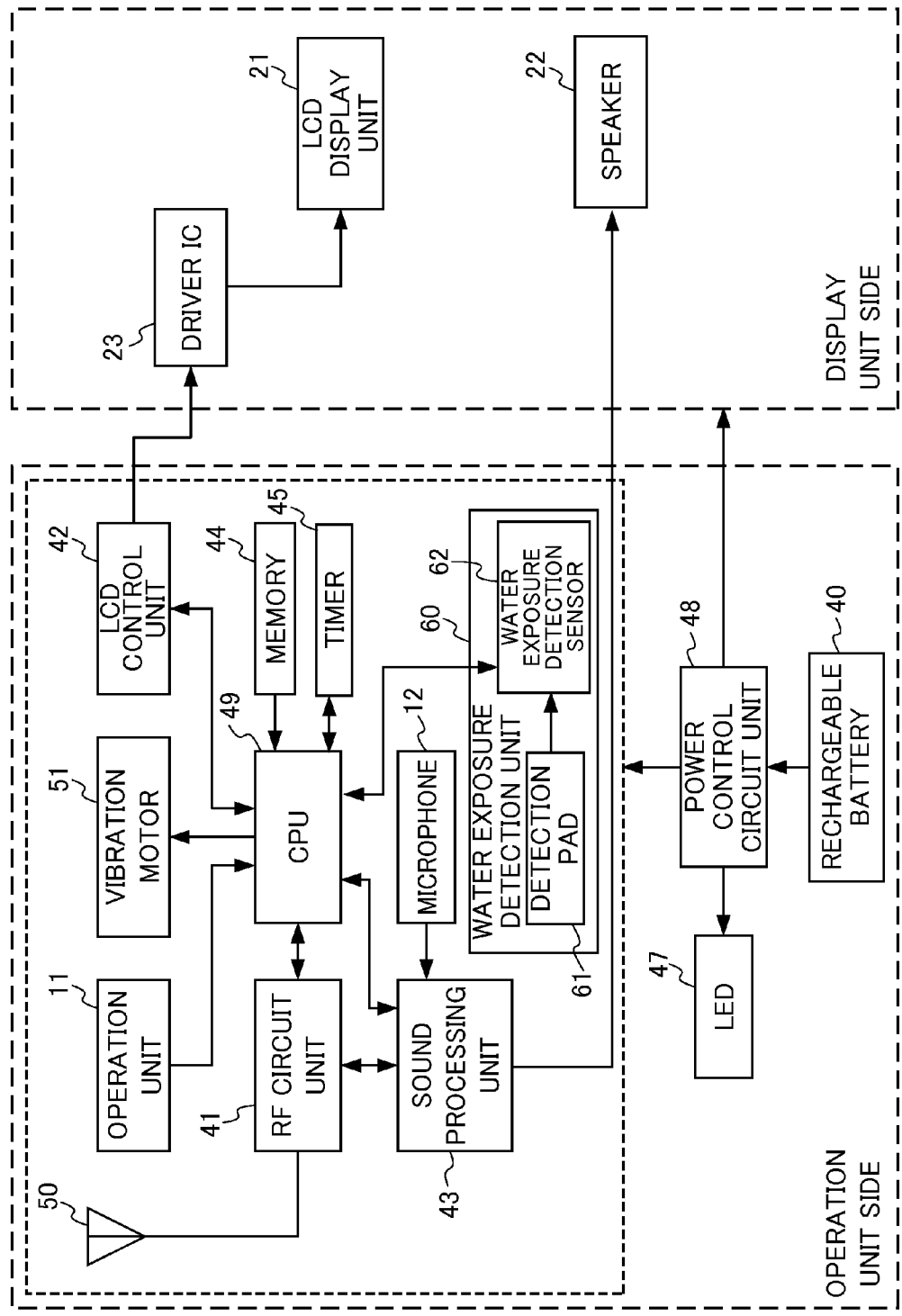
FIG. 4 is a block diagram showing features of the cellular telephone 1.

FIG. 4 is a block diagram showing features of the cellular telephone 1. The cellular telephone 1 includes the operation unit 11, the microphone 12, the main antenna 50, an RF (Radio Frequency) circuit unit 41, an LCD control unit 42, a sound processing unit 43, memory 44, a timer 45, an LED (Light Emitting Diode) 47, a power control circuit unit 48, the CPU 49 (control unit), a vibration motor 51, the rechargeable battery 40, and the water exposure detection unit (detection unit) 60 that are provided in the operation unit side body 2. In addition, the cellular telephone 1 includes the LCD display unit 21, the speaker 22, and a driver IC 23 that are provided in the display unit side body 3.

The main antenna 50 communicates with external devices by using a predetermined usable frequency band (for example, 800 MHz). It should be noted that, although the predetermined usable frequency band is set to 800 MHz in the present embodiment, other frequency bands can also be used. Moreover, the main antenna 50 can be configured as a so-called dual band compatible antenna that can accept, in addition to the predetermined usable frequency band, another usable frequency band (for example, 2 GHz).

The RF circuit unit 41 performs demodulation processing of a signal received by the main antenna 50 and supplies the processed signal to the CPU 49. In addition, the RF circuit unit 41 performs modulation processing of a signal supplied from the CPU 49, and submits the processed signal to an external device (base station) via the main antenna 50. On the other hand, the RF circuit unit 41 notifies strength of the signal received by the main antenna 50 to the CPU 49.

The LCD control unit 42 performs predetermined image processing according to control by the CPU 49, and outputs image data thus processed to the driver IC 23. The driver IC 23 stores the image data supplied from the LCD control unit 42 in frame memory, and outputs to the LCD display unit 31 at a predetermined timing.

The sound processing unit 43 performs predetermined sound processing with respect to the signal supplied from the RF circuit unit 41 according to control by the CPU 49, and outputs the signal thus processed to the speaker 22. The speaker 22 outputs the signal submitted from the sound processing unit 43 to the outside.

In addition, the sound processing unit 43 processes the signal being input from the microphone 12 according to control by the CPU 49 and outputs the signal thus processed to the RF circuit unit 41. The RF circuit unit 41 performs predetermined processing with respect to the signal submitted from the sound processing unit 43 and outputs the signal thus processed to the main antenna 50.

The memory 44 includes, for example, working memory and is used for arithmetic processing by the CPU 49. More specifically, capacitance detected by the water exposure detection unit 60 (described later), predetermined thresholds and the like can be stored therein. The memory 44 can double as a detachable external memory.

The timer 45 has a time keeping function and is configured to be able to output time information including current time to the CPU 49. The timer 45 notifies the CPU 49 that a preset time period has elapsed. In addition, the timer 45 is configured such that power supply is maintained to operate the time keeping function, even in a state in which power source of the cellular telephone 1 is interrupted. Although the time 45 is disposed outside of the CPU 49 in the present embodiment, a timer can be embedded in the CPU 49.

The LED 47 is configured to emit light based on a voltage supplied from the power control circuit unit 48.

The power control circuit unit 48 is connected to the rechargeable battery 40, converts source voltage supplied from the rechargeable battery 40 to a predetermined source voltage, and supplies the source voltage thus converted to the LED 47 and the like. It is obvious that the power control circuit unit 48 supplies power to other electronic component, functional blocks and the like as well.

When the RF circuit unit 41 detects an incoming call signal to the cellular telephone 1, the LCD display unit 21, the LED 47, the vibration motor 51 and the speaker 22 are activated to notify an incoming call. When a responding operation is made to the incoming call, the RF circuit unit 41 is shifted to communication and conversation.

The water exposure detection unit 60 is provided with the detection pad 61 and the detection sensor 62. The water exposure detection unit 60 detects capacitance, which is a physical quantity that changes according to a water-exposed state.

The detection pad 61 is disposed on the circuit board 30 and configured to change capacitance according to contact with water.

The detection sensor 62 is configured to include a detection circuit that detects capacitance of the detection pad 61. The detection sensor 62 monitors the detection pad 61 for a certain period of time or constantly, thereby detecting a change in capacitance of the detection pad 61 according to contact with water. The detection sensor 62 then notifies the capacitance thus detected to the CPU 49.

The CPU 49 controls the entire cellular telephone 1. In addition, the CPU 49 monitors an internal state such as a signal state of the main antenna 50, a level of the rechargeable battery 40, presence of missed calls and unread mail, and the like, and performs control such as changing of the emission color of LED 47 and display content of the LCD display unit 21 based on results of monitoring. Furthermore, the CPU 49 controls the power control circuit unit 48 to interrupt power supply according to the detection result from the water exposure detection unit 60.

More specifically, the CPU 49 determines minor water exposure in a case in which the capacitance detected by the water exposure detection unit 60 is at least a threshold A (the first threshold value) and less than a threshold B (the second threshold value) that is greater than the threshold A, and controls the power control circuit unit 48 to continue interruption of the power supply until time T1 (the first predetermined time period) elapses.

In addition, the CPU 49 determines major water exposure in a case in which the capacitance detected by the water exposure detection unit 60 is at least the threshold B, and controls the power control circuit unit 48 to continue interruption of the power supply until time T2 (the second predetermined time period), which is longer than the time T1, elapses. Here, elapse of the time T1 or T2 is determined by the timer 45, which starts time keeping upon interruption of the power supply and notifies the elapse of the time T1 or time T2 to the CPU 49.

The cellular telephone 1 of the present embodiment thus configured can be controlled to interrupt the power supply until the time T1 or T2 elapses, according to the value of capacitance detected. The cellular telephone 1 can thus avoid a short circuit of the electronic parts installed on the circuit board 30, and can change the duration of interruption of power supply according to whether the water-exposed state of the circuit board 30 is a minor water exposure or a major water exposure.

As used in the present embodiment, the minor water exposure is a case where dew condensation is caused on the circuit board 30 by rise in environmental temperature from a low temperature to a normal temperature, or where the circuit board 30 gets wet due to the cellular telephone 1 being exposed to rain and the like. On the other hand, the major water exposure is a case where water is poured on the cellular telephone 1 or where the circuit board 30 gets wet due to the cellular telephone being submerged in water.

In addition, as used in the present embodiment, the first water-exposed state is a state in which dew condensation is caused on the circuit board 30 by rise in environmental temperature from a low temperature to a normal temperature, or in which the circuit board 30 gets wet due to the cellular telephone 1 being exposed to rain and the like. On the other hand, the second water-exposed state is a state in which water is poured on the cellular telephone 1 or where the circuit board 30 gets wet due to the cellular telephone being submerged in water.

Thereafter, in a case in which the capacitance detected by the water exposure detection unit 60 is at least the threshold A and less than the threshold B, the CPU 49 controls the LCD display unit 21 to display information (the first mode) to notify the user of the minor water exposure of the circuit board 30 and the interruption of the power supply of the cellular telephone 1.

In addition, in a case in which the capacitance detected by the water exposure detection unit 60 is at least the threshold B, the CPU 49 controls the LCD display unit 21 to display information (the second mode) to notify the user of the major water exposure of the circuit board 30 and the interruption of the power supply of the cellular telephone 1.

After notification in the first or second mode, the CPU 49 controls the power control circuit unit 48 to interrupt the power supply.

The cellular telephone 1 of the present embodiment thus configured can notify the user in the first or second mode, according to the value of capacitance detected by the water exposure detection unit 60. The user can thus recognize whether the minor water exposure or the major water exposure has occurred to the cellular telephone 1.

Furthermore, the CPU 49 can control the power control circuit unit 48 to supply power after the time T1 or T2 elapses.

The cellular telephone 1 of the present embodiment can thus be made available again after a predetermined time period that is considered to be enough for drying the circuit board 30 in the water-exposed state, by supplying power after the time T1 or T2 elapses.

In addition, the CPU 49 detects capacitance by the water exposure detection unit 60 after the time T1 or T2 elapses. Furthermore, the CPU 49 can control the power control circuit unit 48 to supply power in a case in which the capacitance detected by the water exposure detection unit 60 is less than the threshold A.

As described above, the cellular telephone 1 of the present embodiment detects the capacitance again after the time T1 or T2 elapses. By confirming, by the capacitance thus detected, that the circuit board 30 in the water-exposed state has dried, and then supplying power again, the user can use the cellular telephone 1 in a safe state.

Figure 5:
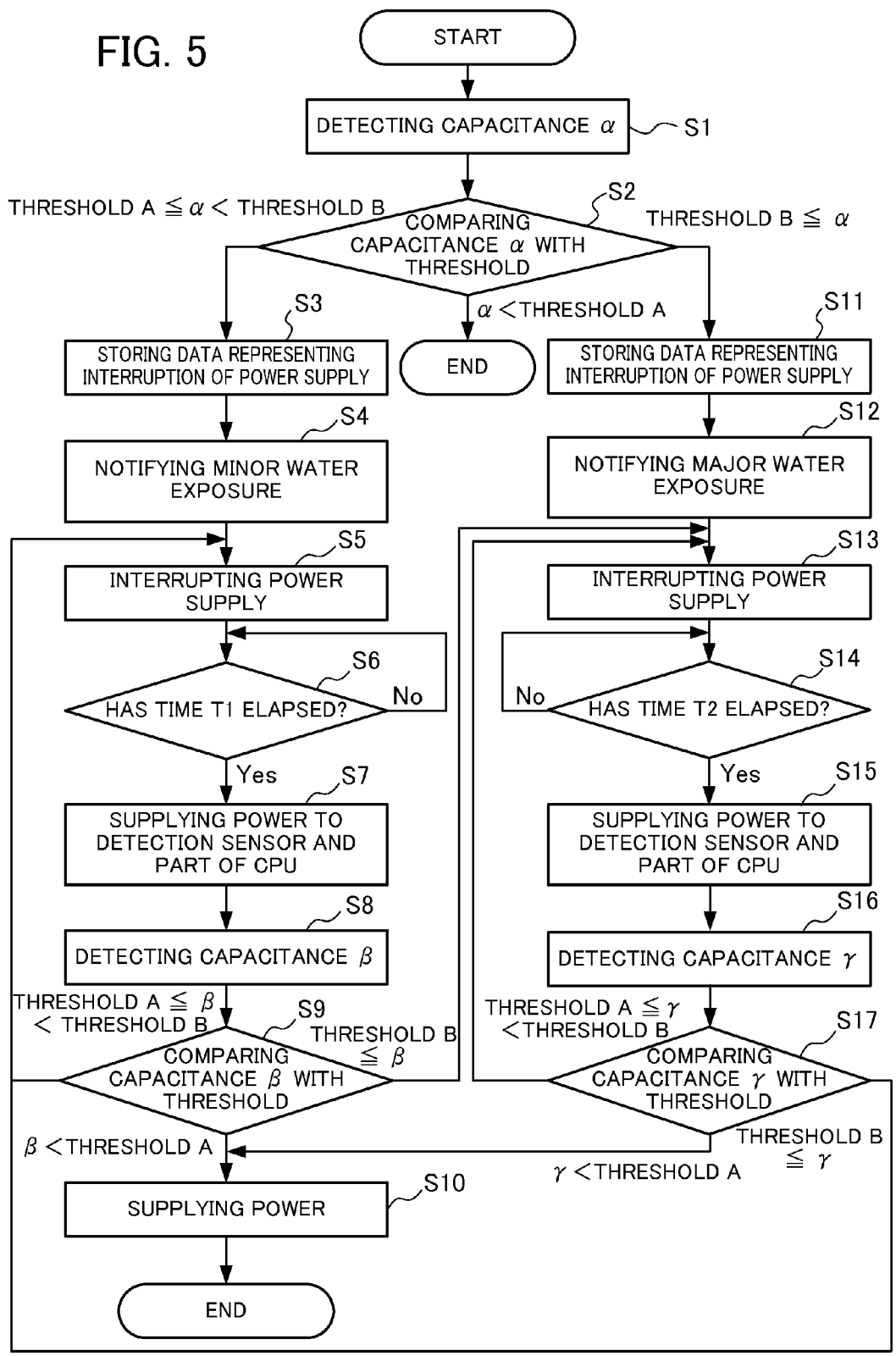
FIG. 5 is a flow chart showing a flow of processing of the cellular telephone 1.

Next, a flow of processing of the cellular telephone device 1 of the present embodiment is described with reference to FIG. 5. FIG. 5 is a flow chart showing a flow of processing of the cellular telephone 1.

In Step S1, the detection sensor 62 detects the changed capacitance α in the detection pad 61, and then notifies the capacitance α thus detected to the CPU 49.

In Step S2, the CPU 49 compares the capacitance α detected by the detection sensor 62 with the threshold A and the threshold B. In a case in which the capacitance α is at least the threshold A and less than the threshold B (threshold A≦capacitance α<threshold B), the processing advances to Step S3. In a case in which the capacitance α is at least the threshold B, (threshold B≦capacitance α), the processing advances to Step S11. On the other hand, in a case in which the capacitance α is less than the threshold A, (capacitance α<threshold A), the detection pad 61 is determined not to be in a water-exposed state, and the processing is terminated.

In Step S3, the CPU 49 stores data representing the interruption of power supply due to minor water exposure of the circuit board 30 to the memory 44.

In Step S4, the CPU 49 controls the LCD display unit 21 to display information (for example, a string "Minor water exposure detected. Automatic power off.") to notify the user of the minor water exposure of the circuit board 30 and the interruption of the power supply of the cellular telephone 1.

In Step S5, the CPU 49 controls the power control circuit unit 48 to interrupt the power supply. Upon interruption of the power supply, the CPU 49 starts time keeping by the timer 45. Here, a part of the CPU 49 is still active after interruption of the power supply, and receives notification of elapse of the time from the timer 45.

In Step S6, the CPU 49 determines whether the time T1 has elapsed since the interruption of the power supply in Step S5, by time keeping by the timer 45. In a case where the time T1 has elapsed since the interruption of the power (Yes determination), the processing advances to Step S7. On the other hand, in a case where the time T1 has not elapsed since the interruption of the power (No determination), the processing advances to Step S6.

In Step S7, the CPU 49 controls the power control circuit unit 48 to supply power to the water exposure detection unit 60 and to a part of the CPU 49 controlling the water exposure detection unit 60. The water exposure detection unit 60 and the part of the CPU 49 controlling the water exposure detection unit 60 are thus made operable.

In Step S8, the detection sensor 62 detects the changed capacitance β in the detection pad 61, and then notifies the capacitance β thus detected to the CPU 49.

In Step S9, the CPU 49 compares the capacitance β detected by the detection sensor 62 with the threshold A and the threshold B. In a case in which the capacitance β is at least the threshold A and less than the threshold B (threshold A≦capacitance β<threshold B), the processing advances to Step S5. In a case in which the capacitance β is at least the threshold B, (threshold B≦capacitance β), the processing advances to Step S13. In a case in which the capacitance β is less than the threshold A, (capacitance β<threshold A), the processing advances to Step S10.

In Step S10, the CPU 49 controls the power control circuit unit 48 to supply power and activates the cellular telephone 1.

In Step S11, the CPU 49 stores data representing the interruption of power supply due to major water exposure of the circuit board 30 to the memory 44.

In Step S12, the CPU 49 controls the LCD display unit 21 to display information (for example, a string "Major water exposure detected. Automatic power off.") to notify the user of the major water exposure of the circuit board 30 and the interruption of the power supply of the cellular telephone 1.

In Step S13, the CPU 49 controls the power control circuit unit 48 to interrupt the power supply. Upon interruption of the power supply, the CPU 49 starts time keeping by the timer 45. Here, a part of the CPU 49 is still active after interruption of the power supply, and receives notification of elapse of the time from the timer 45.

In Step S14, the CPU 49 determines whether the time T2 has elapsed since the interruption of the power supply in Step S13, by time keeping by the timer 45. In a case where the time T2 has elapsed since the interruption of the power (Yes determination), the processing advances to Step S15. On the other hand, in a case where the time T2 has not elapsed since the interruption of the power (No determination), the processing advances to Step S14.

In Step S15, the CPU 49 controls the power control circuit unit 48 to supply power to the water exposure detection unit 60 and to a part of the CPU 49 controlling the water exposure detection unit 60. The water exposure detection unit 60 and the part of the CPU 49 controlling the water exposure detection unit 60 are thus made operable.

In Step S16, the detection sensor 62 detects the changed capacitance γ in the detection pad 61, and then notifies the capacitance γ thus detected to the CPU 49.

In Step S17, the CPU 49 compares the capacitance γ detected by the detection sensor 62 with the threshold A and the threshold B. In a case in which the capacitance γ is at least the threshold A and less than the threshold B (threshold A≦capacitance γ<threshold B), the processing advances to Step S13 where the power supply is interrupted again. In a case in which the capacitance γ is at least the threshold B, (threshold B≦capacitance γ), the processing advances to Step S5. In a case in which the capacitance γ is less than the threshold A, (capacitance γ<threshold A), the processing advances to Step S10.

Modification

Figure 6:
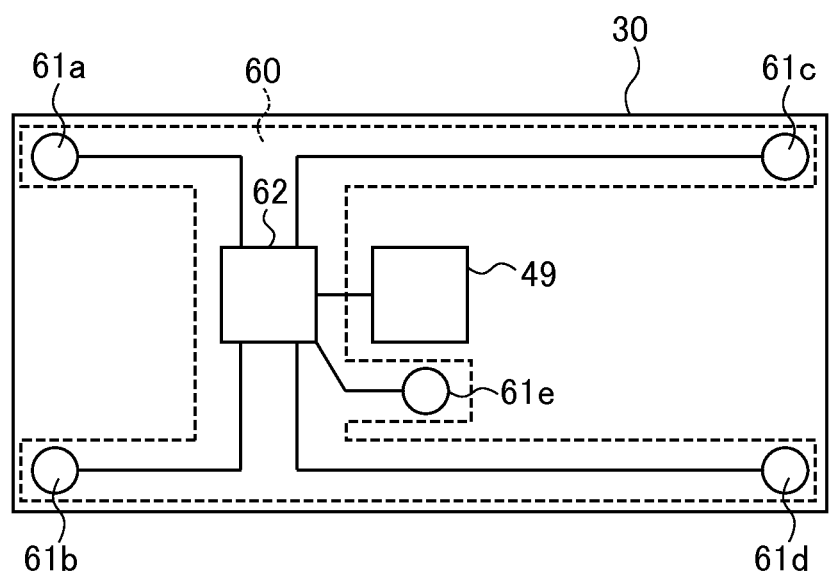
FIG. 6 is a plan view showing a configuration of a circuit board 30 of a Modification.

A modification of the above-described embodiment is hereinafter described with reference to FIG. 6. As shown in FIG. 6, on the circuit board 30 of the modification, the CPU 49 and the water exposure detection unit 60 are installed. The water exposure detection unit 60 is configured to include detection pads 61a, 61b, 61c, 61d and 61e and the detection sensor 62. In other words, in the modification, the water exposure detection unit 60 includes the plurality of detection pads 61a, 61b, 61c, 61d and 61e, each of which is installed on the circuit board 30.

The CPU 49 determines that the circuit board 30 is in the water-exposed state in a case in which the detection sensor 62 detects a maximum value or an average value of a change in capacitance in the detection pads.

By providing the plurality of detection pads 61a, 61b, 61c, 61d and 61e on the circuit board 30, the cellular telephone 1 can determine the water-exposed state of the circuit board 30 more reliably.

In addition, the CPU 49 can be configured to determine dew condensation in a case in which capacitance detected by the water exposure detection unit 60 changes in all of the plurality of detection pads 61a, 61b, 61c, 61d and 61e, and determine waterlog in a case in which the capacitance changes in a part of the plurality of detection pads.

In a case of dew condensation, the circuit board 30 is evenly covered with water drops and capacitance is expected to change in all the detection pads 61. Given this, the CPU 49 determines dew condensation in a case in which a change in capacitance is detected in all of the detection pads. On the other hand, in a case of waterlog, water seeps into the operation unit side body 2 gradually through gaps, and a change in capacitance is expected in a part of the plurality of detection pads on the circuit board 30. Given this, the CPU 49 determines waterlog in a case in which a change in capacitance is detected in a part of the detection pads.

In the cellular telephone 1 of the modification, the CPU 49 can thus determine whether the water-exposed state of the circuit board 30 is dew condensation or waterlog.

Although the embodiments of the present invention have been described above, the present invention is not limited to the aforementioned embodiments, and alterations are possible as appropriate.

In the above embodiments, the LCD display unit 21 is used as the notification unit to notify a user of water exposure; however, the present invention is not limited thereto. For example, the vibration motor 51 can be used as the notification unit in such a configuration that the vibration motor 51 is controlled to vibrate in a first mode to notify minor water-exposed state and in a second mode to notify major water-exposed state different from the first mode. The cellular telephone 1 can thus notify the user of the minor water-exposed state and the major water-exposed state by vibration of the vibration motor 51.

Alternatively, the speaker 22 can be used as the notification unit in such a configuration that the speaker 22 is controlled to output sound or voice in a first mode to notify minor water-exposed state and in a second mode to notify major water-exposed state different from the first mode. The cellular telephone 1 can thus notify the user of the minor water-exposed state and the major water-exposed state by sound or voice.

In addition, in the above embodiments, the detection pad 61 is installed on a face of the circuit board 30 on which the CPU 49 and the like are installed; however, the present invention is not limited thereto. For example, the detection pad 61 can also be installed on a face of the circuit board 30 that is opposite to the face on which the CPU 49 and the like are installed.

In addition, in the above embodiments, the detection pad 61 is installed on the circuit board 30 in the operation unit side body 2; however, the present invention is not limited thereto. For example, the detection pad 61 can also be installed on a circuit board in the display unit side body 3.

In addition, in the above embodiments, the detection pads 61a, 61b, 61c, and 61d are installed in end portions of the circuit board 30 and the detection pad 61e is installed in the vicinity of the CPU 49; however, the arrangement of the detection pads is not limited thereto. For example, the detection pads can also be installed in the vicinity of a connector part of the operation unit side body 2, through which water can seep thereinto. In such a configuration, the cellular telephone 1 can detect water exposure more preferably. Furthermore, the number of the detection pad(s) is not particularly limited.

In addition, in the above embodiments, the detection unit 60 detects water exposure by change in capacitance; however, the present invention is not limited thereto. For example, the detection unit 60 can be configured to directly detect water exposure, to determine whether the water exposure is dew condensation or waterlog, and to notify the CPU 49 with a result of the determination.

In addition, in the above embodiments, the detection unit 60 determines a degree of water exposure by detecting change in capacitance; however, the present invention is not limited thereto and the degree of water exposure can be determined by using a water detection unit as another detection unit.

More specifically, the water detection unit irradiates a detection pad with infrared light having a wavelength adjusted to correspond to an energy absorption band of water from a light emitting portion, and receives the infrared light from the detection pad in a light receiving portion. The energy intensity of the infrared light received in the light receiving portion changes depending on presence or absence of water molecules on the detection pad and the amount thereof. Therefore, the degree of the water-exposed state can be determined from an amount of change in the energy intensity between the light emitting portion and the light receiving portion of the infrared light, detected by a detection sensor. For example, as the amount of change in the energy intensity, a case in which the energy intensity in the light receiving portion is less than 85% of that in the light emission portion can be defined as the first water-exposed state. On the other hand, a case in which the energy intensity in the light receiving portion is at least 85% and less than 95% of that in the light emission portion can be defined as the second water-exposed state.

The detection pad is preferably composed of, for example, glass that transmits 99% of infrared light. The energy intensity received in the light receiving portion changes depending on presence or absence of water molecules and the amount thereof on the glass. As the light emitting portion, an LED that emits infrared light can be exemplified. As the light receiving portion, a light sensor using photodiodes can be exemplified.

It should be noted that, although the cellular telephone 1 has been described in the above embodiments, the present invention is not limited thereto and may be PHS (Personal Handyphone System), a PDA (Personal Digital Assistant), a portable navigation apparatus, a portable personal computer such as a laptop computer, and the like.

EXPLANATION OF REFERENCE NUMERALS

1 Cellular telephone
21 LCD display unit
22 Speaker
48 Power control circuit unit
49 CPU
51 Vibration motor
60 Water exposure detection unit
61 Detection pad
62 Detection sensor

The invention claimed is:

1. An electronic device comprising:
   a detection unit that detects a physical quantity that changes according to a water-exposed state; and
   a control unit that interrupts power supply until a first predetermined time period elapses, in a case in which the physical quantity detected by the detection unit is at least a first threshold value and less than a second threshold value, and interrupts the power supply until a second predetermined time period, which is longer than the first predetermined time period, elapses, in a case in which the physical quantity detected by the detection unit is at least the second threshold value.

2. The electronic device according to claim 1, further comprising a notification unit that makes a notification in a first mode in a case in which the physical quantity detected by the detection unit is at least the first threshold value and less than the second threshold value, and makes a notification in a second mode in a case in which the physical quantity detected by the detection unit is at least the second threshold value,
   wherein the control unit interrupts power supply after the notification in the first or second mode by the notification unit.

3. The electronic device according to claim 1,
wherein the control unit prevents interruption of the power supply after the first predetermined time period or the second predetermined time period elapses.

4. The electronic device according to claim 1, wherein the control unit continues interruption of the power supply in a case in which the physical quantity detected by the detection unit after the first predetermined time period or the second predetermined time period elapses is at least the first threshold value.

5. The electronic device according to claim 1, wherein the detection unit comprises a plurality of detection pads, the physical quantity of each of the detection pads changes according to a water-exposed state and a detection sensor that detects a change in the physical quantity of each of the plurality of detection pads.

6. The electronic device according to claim 1, wherein the physical quantity is capacitance.

7. An electronic device comprising:
a detection unit that detects a water-exposed state; and
a control unit that interrupts power supply until a first predetermined time period elapses in a case in which the detection unit detects a first water-exposed state and interrupts power supply until a second predetermined time period, which is longer than the first predetermined time period, elapses, in a case in which the detection unit detects a second water-exposed state, which is greater in degree of the water-exposed state than a first water-exposed state.

8. The electronic device according to claim 7, further comprising a notification unit that makes a notification in a first mode in a case in which the detection unit detects the first water-exposed state, and makes a notification in a second mode in a case in which the detection unit detects the second water-exposed state, wherein the control unit interrupts power supply after the notification in the first or second mode by the notification unit.

9. The electronic device according to claim 7, wherein the control unit prevents interruption of the power supply after the first predetermined time period or the second predetermined time period elapses.

10. The electronic device according to claim 7, wherein the control unit continues interruption of the power supply in a case in which the detection unit detects the first or second water-exposed state after the first predetermined time period or the second predetermined time period elapses.

11. The electronic device according to claim 7, wherein the detection unit comprises a plurality of detection pads, the physical quantity of each of the detection pads changes according to water-exposed state and a detection sensor that detects a change in the physical quantity of each of the plurality of detection pads.

12. The electronic device according to claim 11, wherein the first water-exposed state is a state in which a change in the physical quantity is detected by the detection sensor in all of the plurality of detection pads, and the second water-exposed state is a state in which a change in the physical quantity is detected by the detection sensor in a part of the plurality of detection pads.

* * * * *